US008311600B2

(12) United States Patent
Katura et al.

(10) Patent No.: US 8,311,600 B2
(45) Date of Patent: Nov. 13, 2012

(54) OPTICAL MEASUREMENT INSTRUMENT FOR LIVING BODY (75) Inventors: Takusige Katura, Tokyo (JP); Naoki Tanaka, Tokyo (JP); Atsushi Maki, Fuchu (JP)

(73) Assignee: Hitachi, Ltd., Tokyo (JP)

( * ) Notice: Subject to any disclaimer, the term of this patent is extended or adjusted under 35 U.S.C. 154(b) by 1307 days.

(21) Appl. No.: 11/954,627

(22) Filed: Dec. 12, 2007

(65) Prior Publication Data

US 2008/0146901 A1  Jun. 19, 2008

(30) Foreign Application Priority Data

Dec. 15, 2006  (JP) ................................. 2006-337737

(51) Int. Cl.
*A61B 5/1455* (2006.01)
(52) U.S. Cl. ......................... 600/323; 600/340; 600/322
(58) Field of Classification Search .................. 600/310, 600/322, 323, 326, 328, 336, 481, 473, 476; 356/39–41
See application file for complete search history.

(56) References Cited

U.S. PATENT DOCUMENTS

| | | | | |
|---|---|---|---|---|
| 4,753,246 A | * | 6/1988 | Freeman | 600/544 |
| 6,701,170 B2 | * | 3/2004 | Stetson | 600/323 |
| 2004/0039267 A1 | * | 2/2004 | Kawasaki et al. | 600/310 |
| 2004/0106856 A1 | | 6/2004 | Kimura | |
| 2004/0171919 A1 | * | 9/2004 | Maki et al. | 600/323 |
| 2006/0006343 A1 | | 1/2006 | Tanaka et al. | |
| 2007/0142719 A1 | * | 6/2007 | Kawasaki et al. | 600/336 |

FOREIGN PATENT DOCUMENTS

| | | |
|---|---|---|
| JP | 09-135825 | 5/1997 |
| JP | 2004-173751 | 6/2004 |
| JP | 2005-143609 | 6/2005 |
| WO | WO/2005/046483 | * 5/2005 |

OTHER PUBLICATIONS

"Noisy time-delayed decorrelation and its application to extraction of neural activity from single optical recordings in the guinea pigs" by Ryosuke Hirosaka, et al., Physica D 194 (2004) 320-332.
"Practically of wavelength selection to improve signal-to-noise ratio in near-infrared spectroscopy" Hiroko Sato, et al., NeuroImage 21 (2004)1554-1562.
"Noninvasive measurement of neuronal activity with near-infrared optical imaging" M. Franceschini, et al., NeuroImage 21 (2004) 372-386.

* cited by examiner

*Primary Examiner* — Eric Winakur
*Assistant Examiner* — Chu Chuang (JJ) Liu
(74) *Attorney, Agent, or Firm* — Mattingly & Malur, PC (57) ABSTRACT An optical measurement instrument for living body includes: a plurality of light irradiation means for irradiating an object being tested with light; a plurality of light reception means for detecting the light that is irradiated to the object being tested and propagates inside the object being tested; and a calculation unit for calculating hemodynamics of a plurality of factors inside the object being tested from the detection signal detected by the light reception means, wherein the calculation unit includes a separation calculation unit for separating a plurality of signals from the detection signals; a selection unit for calculating a correlation coefficient between a plurality of the signals separated to select a signal in which a correlation coefficient is a predetermined value or greater as a noise signal; and a reconstruction calculation unit for reconfiguring the detection signal excluding the noise signal selected by the selection unit.

7 Claims, 5 Drawing Sheets

OPTICAL MEASUREMENT INSTRUMENT FOR LIVING BODY

INCORPORATION BY REFERENCE

The present application claims priority from Japanese application JP2006-337737 filed on Dec. 15, 2006, the content of which is hereby incorporated by reference into this application.

BACKGROUND OF THE INVENTION

The present invention relates to an optical measurement technology, and particularly to an optical measurement method and instrument for receiving optical signals from a living body to obtain information on the living body. More particularly, the present invention relates to removing noise signals superimposed on the information on the living body to highly precisely obtain desired living body signals.

Besides targeted signals, there are also noise signals, which are caused by several factors, included in measurement signals that are obtained by measuring information inside the living body using light (e.g., Patent Document 1). An averaging method, a band-pass filter, and the like are used to reduce the effects from the noise signals.

A technique using the averaging method reduces the noise signals based on a precondition that a brain activity responds to the same assignment in the same manner.

A technique using the band-pass filter reduces the noise signals based on a precondition that a brain activity signal and a noise signal exist in different frequency bands. These techniques process a plurality of noise signals. However, a technique is also proposed that is specialized in processing noise signals caused by special factors.

For example, noise signals caused by pulsations (pulsation noise signals) can be reduced by means of a band-cut filter, because their frequency is readily identified. A technique is proposed that reduces pulsation noise signals included in optical measurement signals based on the pulsation signals measured at an area, such as an ear (Patent Document 2). A technique is also proposed that reduces effects from the pulsation noise signals by extracting the pulsation noise signals from the optical measurement signals themselves (Non-Patent Document 1).

Moreover, a technique is also proposed that divides optical measurement signals measured at many points into a plurality of signals by a signal analysis method, and extracts noise signals and target signals (Patent document 3).
[Patent Document 1] JP-A-09-135825
[Patent Document 2] JP-A-2004-173751
[Patent Document 3] JP-A-2005-143609
[Non-Patent Document 1] Maria Angela Franceschini et al., NeuroImage 21 (2004) 372-386
[Non-Patent Document 2] Sato et al., NeuroImage 21 (2004) 1554-1562
[Non-Patent Document 3] Hirosaka et al., Physica D 194 (2004), Pages 320-332

SUMMARY OF THE INVENTION

However, when the noise signals show a similar variation as the target biological signals, conventional techniques have not been capable of removing the noise signals.

When a subject being tested is given a certain task in order to obtain a desired biological signal, for example, when the subject being tested is asked to make a simple voluntary movement at a given time, a displacement in an area being tested caused by the voluntary movement could lead to the noise. At this time, the noise signals superimposed on a desired biological signal very likely show changes similar to those of the desired biological signal such as a brain activity signal.

In such a case, the obtained signals can be erroneously interpreted. For example, a noise associated with a body motion, or a body motion noise is among them.

While the occurrence mechanism of the body motion noise is not sufficiently known, changes in the contact state between a measurement interface and the subject being tested caused by the body motion, dynamic changes in the state inside the measurement target caused by the body motion, and the like are conceivable explanations.

When the brain activity induced by the voluntary movement is a targeted signal, the body motion noise synchronizes with the brain activity, the targeted signal. Therefore, it is difficult to separate them. However, it is absolutely necessary to discriminate them.

It should be noted that although it has become likely that a signal separation method, such as an independent component analysis method, can separate these signals, a clear discrimination reference based on which to discriminate between the body motion noise and brain activity is not provided yet.

The present invention is implemented by an optical measurement instrument for a living body that comprises: a plurality of light irradiation means for irradiating an object being tested with light; a plurality of light reception means for detecting the light that is irradiated to the object being tested and propagates inside the object being tested; and a calculation unit for calculating hemodynamics of a plurality of factors inside the object being tested from the detection signal detected by the light reception means, wherein the calculation unit comprises: a separation calculation unit for separating a plurality of signals from the detection signal; a selection unit for calculating a correlation coefficient between a plurality of the signals separated by the separation calculation unit to select a signal in which the correlation coefficient is a predetermined value or greater as a noise signal; and a reconstruction calculation unit for reconfiguring the detection signal excluding the noise signal selected by the selection unit.

A plurality of factors can be detected from optical signals measured through the use of a plurality of light sources. For example, lights of 690 nm and 830 nm can be used to detect oxygenated hemoglobin and deoxygenated hemoglobin (Non-Patent Document 2). The separation calculation unit calculates a plurality of independent components (separation signals) and mixing coefficient matrices that indicate how each of the independent components contributes to a plurality of measurement signals by means of, for example, an independent component analysis method (Non-Patent Document 3). The independent component analysis method can recover original measurement signals from the independent components and mixture coefficient matrices.

The selection unit selects separation signals based on a certain selection criterion. For example, when trying to select noise components from the separation signals separated by the independent component analysis method, the selection unit obtains a correlation coefficient between a plurality of measurement factors for each of the mixture coefficient matrices corresponding to each separation signal that is binarized by the positive and negative of the value, and selects a separation signal indicating a correlation coefficient greater than a certain value as a noise component.

The reconstruction calculation unit uses only the separation signals selected by the selection unit or other separation signals to reconfigures signals. For example, when the separation signals obtained by the independent component analysis are selected as the noise components, the reconstruction calculation unit performs configuration by setting the mixture coefficient matrices of the selected separation components to zero. This allows the noises to be removed.

The present invention allows the noise components, such as the body motion noises that are difficult to be separated and removed, to be separated and removed, and provides signals with few noise components.

Other objects, features and advantages of the invention will become apparent from the following description of the embodiments of the invention taken in conjunction with the accompanying drawings.

DESCRIPTION OF THE EMBODIMENTS

Figure 1:
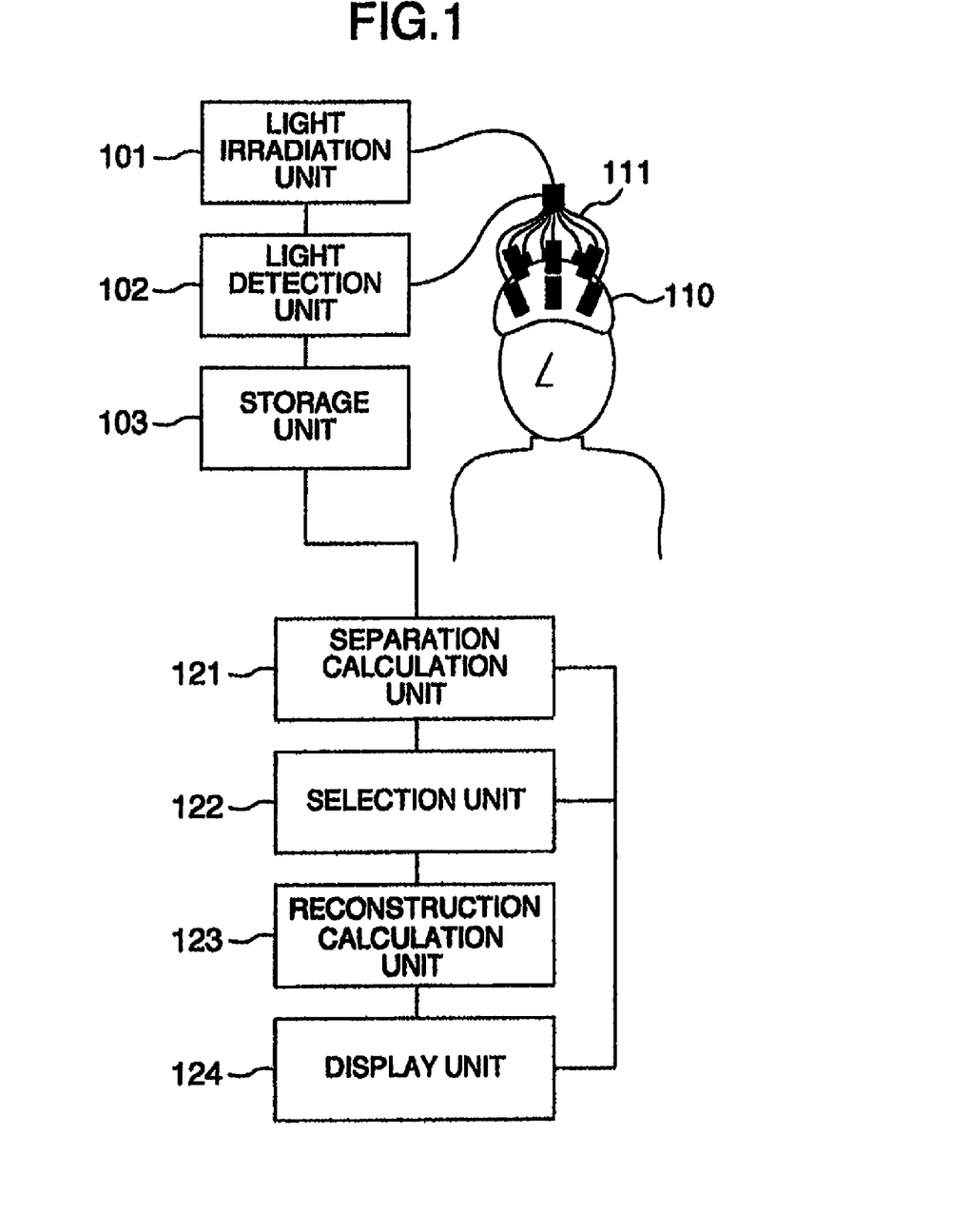
FIG. 1 is a schematic diagram of an embodiment of the present invention.

A specific block diagram is shown in FIG. 1 as an embodiment. An interface unit (110) for optical measurement of a living body is attached to part of or the whole of the head of a subject being tested. A light irradiation unit (101) irradiates the living body with mixed lights of 690 nm and 830 nm wavelengths through an optical fiber (111) coupled to the interface unit (110). The lights of each wavelength, which pass through the living body via the optical fiber (111) coupled to the interface unit (110), are detected by a light detection unit (102), and the detection result is stored in a storage unit (103). Here, light of other wavelengths may also be irradiated, and the number of combination of wavelengths employed may be three or more. Moreover, the obtained optical signals may be employed to the processing described in the following sections, after they are subjected to some sort of calculation processing.

Next, the optical signals are separated by a separation calculation unit (121) based on the method and setting selected by a user. The signals separated by the separation calculation unit (referred to as separation signals) are manually or automatically selected by a selection unit (122) based on the method and setting selected by the user. The signals selected by the selection unit (122) are reconfigured by a reconstruction calculation unit (123) based on the method and setting selected by the user.

A parameter input and a result display of the separation calculation unit, selection unit, and reconstruction calculation unit are performed by a display unit (124). Here, the parameter refers to, for example, a setting value for the signal separation used by the separation calculation unit, and a threshold of the correlation coefficient used by the selection unit.

Figure 2:
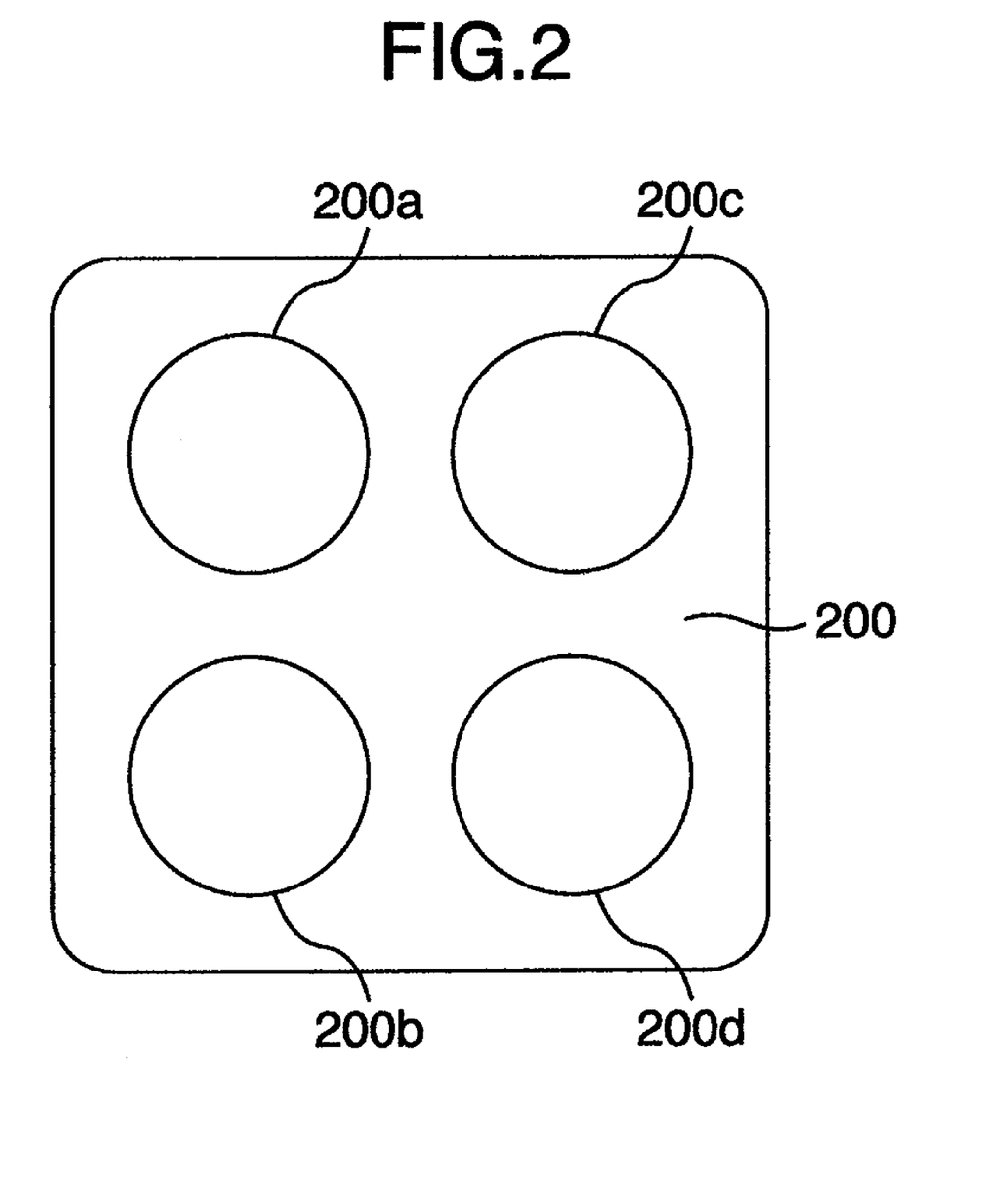
FIG. 2 is an exemplary interface unit in the embodiment.
Figure 3:
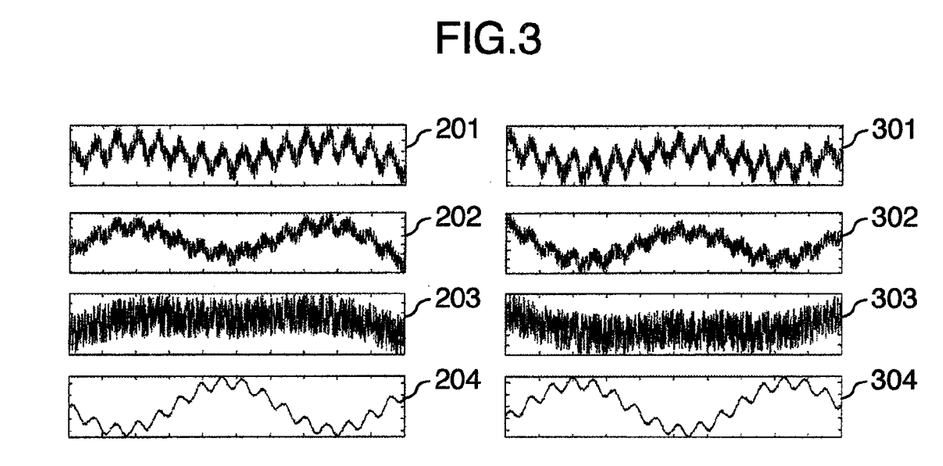
FIG. 3 shows exemplary signals measured by the interface unit of FIG. 2.

Now, detailed description will be provided. First, an example of the interface unit is shown in FIG. 2 as 200. Measure points at this time include a measure point 1 (200$a$), a measure point 2 (200$b$), a measure point 3 (200$c$), and a measure point 4 (200$d$), totaling four points. Here, the measure point refers to a middle point between an irradiation point and a detection point. The present embodiment provides an example in which concentration changes in oxygenated hemoglobin and deoxygenated hemoglobin are calculated from optical signals (Non-Patent Document 2). Examples of signals calculated from the obtained optical signals are shown in FIG. 3. FIG. 3 shows oxygenated hemoglobin concentration changes (201 to 204) measured at four measure points, and deoxygenated hemoglobin concentration changes (301 to 304) measured at the same measure points. A lateral axis indicates time (second), while a vertical axis indicates hemoglobin concentration change amount (mM·mm). These are measurement signals.

Description of reference numerals used in FIG. 3 is as follows.

201 oxygenated hemoglobin concentration changes at a measure point 1
202 oxygenated hemoglobin concentration changes at a measure point 2
203 oxygenated hemoglobin concentration changes at a measure point 3
204 oxygenated hemoglobin concentration changes at a measure point 4
301 deoxygenated hemoglobin concentration changes at a measure point 1
302 deoxygenated hemoglobin concentration changes at a measure point 2
303 deoxygenated hemoglobin concentration changes at a measure point 3
304 deoxygenated hemoglobin concentration changes at a measure point 4

Next, one of the specific calculation techniques performed by the separation calculation unit (121) will be described. A TDD-ICA method (Non-Patent Document 3) may be used as one of the separation techniques. This is one of the techniques referred to as the independent component analysis. A measurement signal X comprised of time series data simultaneously obtained at respective four measure points during the measurement is expressed as follows:

$$X = \begin{bmatrix} x_1(1) & x_1(2) & \ldots & x_1(T) \\ x_2(1) & x_2(2) & \ldots & x_2(T) \\ x_3(1) & x_3(2) & \ldots & x_3(T) \\ x_4(1) & x_4(2) & \ldots & x_4(T) \end{bmatrix} \quad \text{[Expression 1]}$$

wherein T indicates the number of data.

A set of signals comprised of four statistically independent time series signal components (original signal S) is expressed as follows:

$$S = \begin{bmatrix} s_1(1) & s_1(2) & \ldots & s_1(T) \\ s_2(1) & s_2(2) & \ldots & s_2(T) \\ s_3(1) & s_3(2) & \ldots & s_3(T) \\ s_4(1) & s_4(2) & \ldots & s_4(T) \end{bmatrix} \quad \text{[Expression 2]}$$

Assuming that the measurement signal X is expressed in a linear mixing signal that is expressed as follows:

$$X = AS \quad \text{[Expression 3]}$$

in which the set of signals S is multiplied by a mixing coefficient matrix A (indicating to what extent respective original signals S are included in the respective measurement signal X), the mixing coefficient matrix A and original signal S are estimated from only the independent condition of the original signal component and the measurement signal X. Here, the number of samplings refers to the number of data in the time direction. The estimation is performed by whitening and rotation. The whitening means conversion into a linear independent signal by mixture of the measurement signals. It is given using the covariance matrix C of the measurement signal X as follows:

$$X_0 = C^{-1/2} X \quad \text{[Expression 4]}$$

The estimate U of the original signal S comprised of independent components is given as follows by using a proper rotation matrix R:

$$U = R X_0 \quad \text{[Expression 5]}$$

This rotation matrix is determined by the above independence condition. Here, that a delay correlation becomes zero at K delay times $\tau_k$ (k=1, 2, ..., k) is determined as independence. Actually, it is difficult to achieve this. Therefore, minimizing the size of correlation is set as a condition instead. This is achieved by the rotation matrix R that minimizes a loss function expressed by the following expression:

$$L(R) = \sum_{k=1}^{K} \sum_{i \neq j} \left| (R \langle x_0(t) x_0'(t + \tau_k) \rangle_t R')_{ij} \right|^2 \quad \text{[Expression 6]}$$

where x' indicates a dislocation, while $\langle \cdot \rangle_t$ indicates an average time. The estimate W of the mixing coefficient matrix is given by the following expression:

$$W = C^{1/2} R' \quad \text{[Expression 7]}$$

The noise applied to each sensor may be handled as the positive. In such a case, instead of the [expression 3], the following expression is used in which an observation noise is added to the right side thereof.

$$X = AS + N \quad \text{[Expression 8]}$$

At this time, pseudo-whitening is performed instead of whitening, and the pseudo-whitening is performed in the following manner using a covariance matrix G.

$$X_0 = (C - G)^{-1/2} X \quad \text{[Expression 9]}$$

Subsequent processing is the same as the case where sensor noise is not considered. The matrix G must be estimated separately. It is possible to estimate the matrix G from a residual when one section in a rest state is fitted by a polynomial expression. A description has been made as to a case in which the number of measurement points is four. However, the separation calculation can be conducted by the same procedure even when the number of measurement points differs from that.

U: The separation signal and mixing coefficient matrix R are obtained by calculations above mentioned.

Figure 4:
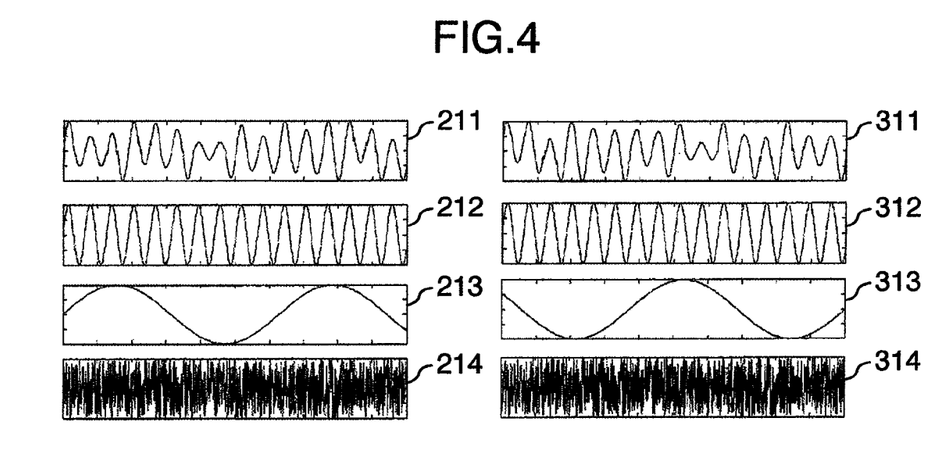
FIG. 4 shows exemplary separation signals calculated by a separation calculation unit.

An example of separation signals is shown in FIG. 4. 211 to 214 are separation signals calculated from the oxygenated hemoglobin concentration changes obtained at four measure points. 311 to 314 are separation signals calculated from deoxygenated hemoglobin concentration changes obtained at four measure points. Description of reference numerals used in FIG. 4 is as follows.

Figure 5:
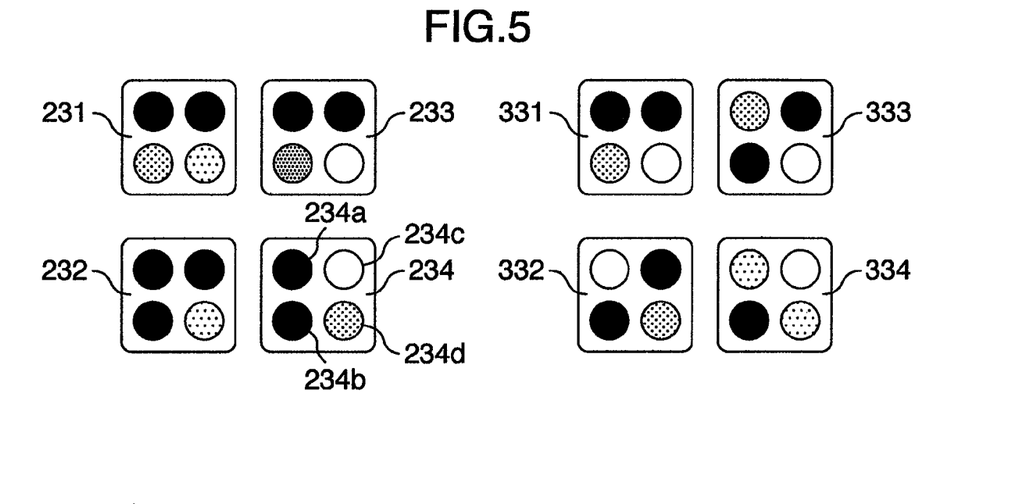
FIG. 5 shows exemplary mixing coefficient matrices calculated by the separation calculation unit.

211 separation signal 1 of oxygenated hemoglobin concentration changes
212 separation signal 2 of oxygenated hemoglobin concentration changes
213 separation signal 3 of oxygenated hemoglobin concentration changes
214 separation signal 4 of oxygenated hemoglobin concentration changes
311 separation signal 1 of deoxygenated hemoglobin concentration changes
312 separation signal 2 of deoxygenated hemoglobin concentration changes
313 separation signal 3 of deoxygenated hemoglobin concentration changes
314 separation signal 4 of deoxygenated hemoglobin concentration changes An example of mixing coefficient matrices is shown in FIG. 5. 231 to 234 indicate the mixing coefficient matrices of 211 to 214, respectively. Color shading indicates the size of the coefficient. Description of reference numerals used in FIG. 5 is as follows.

231 mixing coefficient matrix of the separation signal 1 of oxygenated hemoglobin concentration changes
232 mixing coefficient matrix of the separation signal 2 of oxygenated hemoglobin concentration changes
233 mixing coefficient matrix of the separation signal 3 of oxygenated hemoglobin concentration changes
234 mixing coefficient matrix of the separation signal 4 of oxygenated hemoglobin concentration changes
234a mixing coefficient matrix at a measure point 1 of the separation signal 1 of oxygenated hemoglobin concentration changes
234b mixing coefficient matrix at a measure point 2 of the separation signal 1 of oxygenated hemoglobin concentration changes
234c mixing coefficient matrix at a measure point 3 of the separation signal 1 of oxygenated hemoglobin concentration changes
234d mixing coefficient matrix at a measure point 4 of the separation signal 1 of oxygenated hemoglobin concentration changes
331 mixing coefficient matrix of the separation signal 1 of deoxygenated hemoglobin concentration changes
332 mixing coefficient matrix of the separation signal 2 of deoxygenated hemoglobin concentration changes
333 mixing coefficient matrix of the separation signal 3 of deoxygenated hemoglobin concentration changes
334 mixing coefficient matrix of the separation signal 4 of deoxygenated hemoglobin concentration changes The mixing coefficient matrix 234 of the separation signal 214 will be described in more detail. 234a to 234d correspond to the measure points 1 to 4, respectively. More specifically, it is indicated that the separation signal 214 is strongly mixed at the measure point 2 (234b), and hardly mixed at the measure point 3 (234c).

Here, for highly precise signal separation, filtering processing may be performed before the separation calculation. When the frequency band for a target signal is known, a filtering processing is effective that reduces a frequency band differing from the frequency band for the target signal.

Next, the selection of the separation signals by the selection unit (122) will be described. Here, a case is considered in which a noise related to the motion of a body (not brain activity) is selected. The noise is referred to as a body motion noise hereinafter. In other words, it is a noise that occurs when a body moves. While the occurrence mechanism of the body motion noise is not known sufficiently yet, it is thought that the body motion noise occurs due to a change in the contact state between a measurement interface and a subject to be measured caused by the body motion, a dynamic change in the internal state of the subject to be measured, and the like. When the signal of brain activity evoked by body motion is a target signal, it is extremely difficult to separate the target signal from a body motion signal, because the body motion signal occurs in synchronization with the brain activity as the target signal. However, it is absolutely necessary to discriminate them. For the change with time of the body motion noise, similarity is not guaranteed between different measurement factors (here, oxygenated hemoglobin and deoxygenated hemoglobin). Therefore, it is difficult to select the body motion noise from the correlation of the calculated separation signals.

However, it is thought that the extent of the influence the body motion noise has on each measure point is equal between different measurement factors. Therefore, it is possible to select the body motion noise from the correlation of the calculated mixing coefficient matrices.

Figure 6:
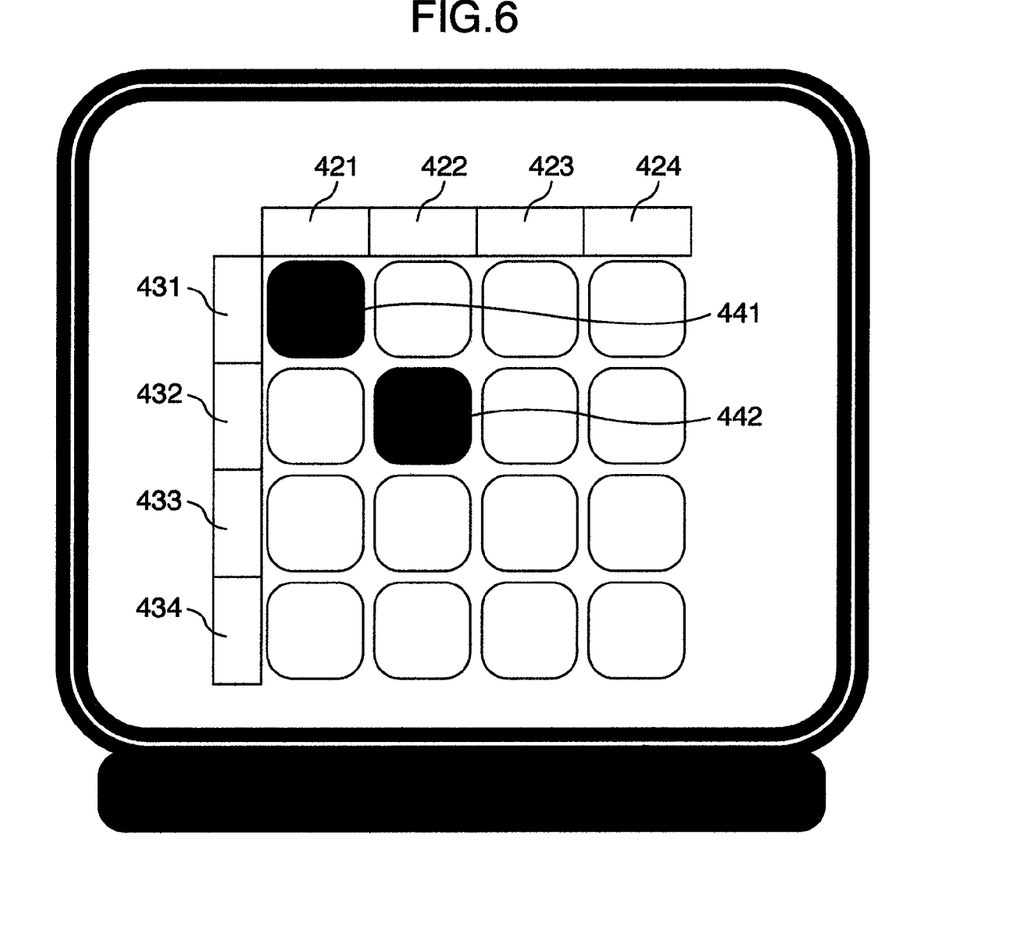
FIG. 6 is an exemplary display of the separation signals as a result of selection by a selection unit using the mixing coefficient matrices.

Accordingly, the correlation between the oxygenated hemoglobin and deoxygenated hemoglobin is calculated from the mixing coefficient matrices shown in FIG. 5, and an example is shown in FIG. 6 in which a correlation coefficient with correlation higher than a certain value (here 0.5) is represented in black, while that with correlation lower than the certain value is represented in white. Description of reference numerals used in FIG. 6 is as follows.

421 column corresponding to the mixing coefficient matrix of the separation signal 1 of oxygenated hemoglobin concentration changes
422 column corresponding to the mixing coefficient matrix of the separation signal 2 of oxygenated hemoglobin concentration changes
423 column corresponding to the mixing coefficient matrix of the separation signal 3 of oxygenated hemoglobin concentration changes
424 column corresponding to the mixing coefficient matrix of the separation signal 4 of oxygenated hemoglobin concentration changes
431 row corresponding to the mixing coefficient matrix of the separation signal 1 of deoxygenated hemoglobin changes
432 row corresponding to the mixing coefficient matrix of the separation signal 2 of deoxygenated hemoglobin changes
433 row corresponding to the mixing coefficient matrix of the separation signal 3 of deoxygenated hemoglobin changes
434 row corresponding to the mixing coefficient matrix of the separation signal 4 of deoxygenated hemoglobin changes
441 correlation coefficient between the mixing coefficient matrix of the separation signal 1 of oxygenated hemoglobin concentration changes and the mixing coefficient matrix of the separation signal 1 of deoxygenated hemoglobin concentration changes that is higher than 0.5 and is represented in black.
442 correlation between the mixing coefficient matrix of the separation signal 2 of oxygenated hemoglobin concentration changes and the mixing coefficient matrix of the separation signal 2 of deoxygenated hemoglobin concentration changes that is higher than 0.5 and is represented in black.

In FIG. 6, column 421 to 424 correspond to the mixing coefficient matrices 231 to 234, respectively, and rows 431 to 434 correspond to the mixing coefficient matrices 331 to 334, respectively. In other words, 441 indicates that the correlation coefficient between the mixing coefficient matrix 231 and the mixing coefficient matrix 331 is greater than 0.5, while 442 indicates that the correlation between the mixing coefficient matrix 232 and the mixing coefficient matrix 332 is greater than 0.5.

Therefore, the result indicates that the separation components 211, 311 and separation components 212, 312 are body motion noises.

Incidentally, it is known that the influence that changes due to the brain activity have on each measure point tends to be similar between the oxygenated hemoglobin and deoxygenated hemoglobin. Therefore, it is likely that the brain activity is also included in the result shown in FIG. 6 in addition to the body motion noises.

Therefore, attention is directed to the difference between the brain activity and body motion noise. In other words, when a certain separation signal is a brain activity, and it exists in a limited area, the mixing coefficient matrix has a high value at a particular measure point (measure point 3 for 233 and 333 in FIG. 5) and has a low value at other measure points. Similarity of each value between oxygenated hemoglobin and deoxygenated hemoglobin is thought to be low at the measure point where the value is low because of the complexity of the living body.

However, since the body motion noise is physically caused, the similarity of the mixing coefficient matrix between the oxygenated hemoglobin and deoxygenated hemoglobin is thought to be high even at the measure point where the value is low.

Therefore, in order to extract the characteristic of the point where the value of the mixing coefficient matrix is low, binarization using the positive and negative of the value is performed. More specifically, binarization is performed using zero as a threshold value. An example of binarized mixing coefficient matrices is shown in FIG. 7. 241 to 244 and 341 to 344 show 231 to 234 and 331 to 334 of FIG. 5 that are binarized, respectively.

Figure 7:
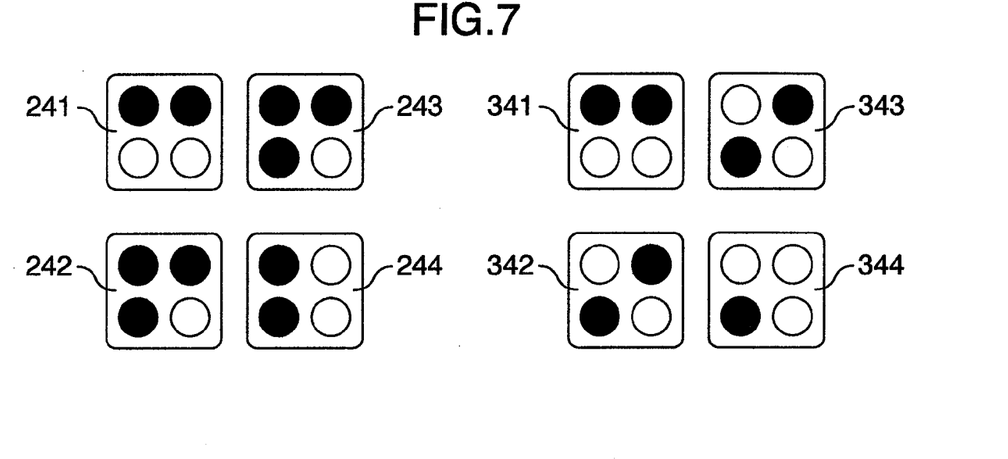
FIG. 7 is an example in which the mixing coefficient matrices calculated by the separation calculation unit are binarized.
Figure 8:
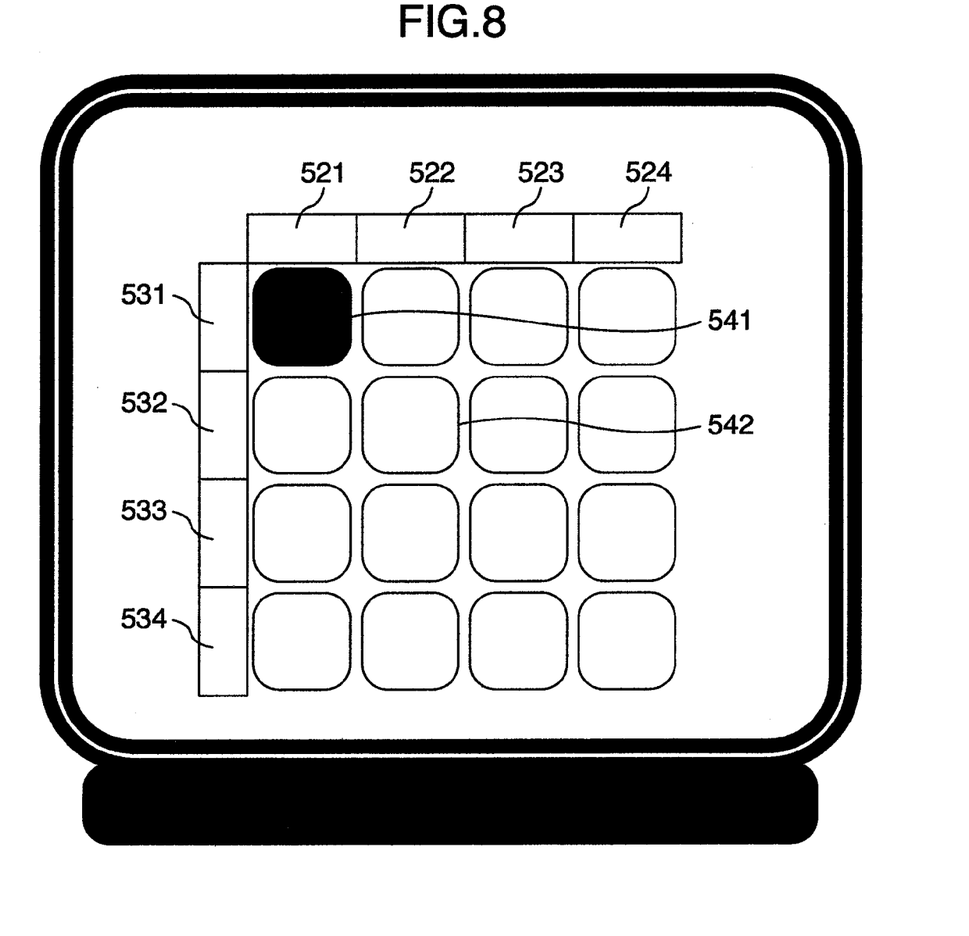
FIG. 8 is an exemplary display of the separation signals as a result of selection by the selection unit using the binarized mixing coefficient matrices.

Description of reference numerals used in FIG. 7 is as follows.
241 binarized mixing coefficient matrix of separation signal 1 of oxygenated hemoglobin concentration changes
242 binarized mixing coefficient matrix of separation signal 2 of oxygenated hemoglobin concentration changes
243 binarized mixing coefficient matrix of separation signal 3 of oxygenated hemoglobin concentration changes
244 binarized mixing coefficient matrix of separation signal 4 of oxygenated hemoglobin concentration changes
341 binarized mixing coefficient matrix of separation signal 1 of deoxygenated hemoglobin concentration changes
342 binarized mixing coefficient matrix of separation signal 2 of deoxygenated hemoglobin concentration changes
343 binarized mixing coefficient matrix of separation signal 3 of deoxygenated hemoglobin concentration changes
344 binarized mixing coefficient matrix of separation signal 4 of deoxygenated hemoglobin concentration changes Correlation coefficients are calculated from these binarized mixing coefficient matrices, and an example of display is shown in FIG. 8 in which correlation coefficients that are greater than a certain threshold (0.5 here) are selected.

Description of reference numerals used in FIG. 8 is as follows.
521 column corresponding to the binarized mixing coefficient matrix of the separation signal 1 of oxygenated hemoglobin concentration changes
522 column corresponding to the binarized mixing coefficient matrix of the separation signal 2 of oxygenated hemoglobin concentration changes 523 column corresponding to the binarized mixing coefficient matrix of the separation signal 3 of oxygenated hemoglobin concentration changes 524 column corresponding to the binarized mixing coefficient matrix of the separation signal 4 of oxygenated hemoglobin concentration changes 531 row corresponding to the binarized mixing coefficient matrix of the separation signal 1 of deoxygenated hemoglobin concentration changes 532 row corresponding to the binarized mixing coefficient matrix of the separation signal 2 of deoxygenated hemoglobin concentration changes 533 row corresponding to the binarized mixing coefficient matrix of the separation signal 3 of deoxygenated hemoglobin concentration changes 534 row corresponding to the binarized mixing coefficient matrix of the separation signal 4 of deoxygenated hemoglobin concentration changes 541 correlation coefficient between the binarized mixing coefficient matrix of the separation signal 1 of oxygenated hemoglobin concentration changes and binarized mixing coefficient matrix of the separation signal 1 of deoxygenated hemoglobin concentration changes that is greater than 0.5 and represented in black 542 correlation coefficient between the binarized mixing coefficient matrix of the separation signal 2 of oxygenated hemoglobin concentration changes and binarized mixing coefficient matrix of the separation signal 2 of deoxygenated hemoglobin concentration changes that is smaller than 0.5 and is represented in white In FIG. 8, in the same way as in FIG. 6, columns 521 to 524 correspond to binarized mixing coefficient matrices 241 to 244, respectively, and rows 531 to 534 correspond to binarized mixing coefficient matrices 341 to 344, respectively. In other words, 541 indicates that the correlation coefficient between the binarized mixing coefficient matrix 241 and the binarized mixing coefficient matrix 341 is greater than a certain value, and 542 indicates that the correlation coefficient between the binarized mixing coefficient matrix 242 and the binarized mixing coefficient matrix 342 is smaller than a certain value.

In FIG. 6, 442 is selected as a body motion noise. However, in FIG. 8, 542 is not selected as the body motion noise. Accordingly, separation signals 212 and 312 are thought to correspond to the brain activity.

This means that the present technique allows the selection of the body motion noise as well as the brain activity noise at the same time.

In the selection of the separation signal, the user may select a body motion noise based on this result or may automatically select it. Although 0.5 is used here as a threshold of the correlation coefficient, other values may be used depending on the measurement signals.

In the present embodiment, selection is made from among all of the separation signals. However, in order to pay attention to a change in an assignment given to the subject being examined during the measurement, the selection unit may extract separation components having high correlation with the time for the assignment in advance to make selection from among the previously extracted separation components.

Furthermore, as an indicator of the similarity to the time for the assignment at this time, synchronism of signal change with the assignment that is performed repeatedly may be used. Specifically, when the assignment is repeated, for example, for five times, measurement signals are extracted at times in synchronization therewith, and a correlation coefficient of the extracted five measurement signal fragments is used as an indicator of the synchronism.

Moreover, while the similarity in binarized mixing coefficient matrix between oxygenated hemoglobin and deoxygenated hemoglobin is used as a selection criterion in the present embodiment, the difference in phase between oxygenated hemoglobin changes and deoxygenated hemoglobin changes during brain activity may be used as the selection criterion. Specifically, an instantaneous phase is calculated through a Hilbert transform or the like, and when the phase difference between oxygenated hemoglobin and deoxygenated hemoglobin is smaller than a certain value, it may be determined that the body motion noise exists, while when the phase difference is in the range of a certain value different from the foregoing value, it may be determined that brain activity exists.

Furthermore, in order to derive the selection criterion, the separation calculation and signal selection are performed by use of all the measurement signals in the present embodiment. However, the separation calculation and signal selection may also be performed by dividing the measurement signals into parts.

In this case, the signal selection may be performed using the result of the separation calculation that is performed for part of a plurality of the measurement signals. The obtained result of a plurality of separation calculations may be grouped by a method, such as clustering, and subsequently each group may be subjected to the selection processing.

Next, the reconstruction calculation unit (123) performs signal reconstruction based on the signal selection performed by the selection unit. Specifically, when the selection is for the purpose of removing noises, zero is substituted into the mixing coefficient matrix of the separation signal, and reconstruction is performed by a reconstruction method using the independent component analysis method. When the selection is for the purpose of extracting a target signal, zero is substituted into the mixing coefficient matrix of an unselected separation signal, and the reconstruction is performed by the reconstruction method using the independent reconstruction analysis method. It should be noted that although 0 is substituted into the mixing coefficient matrix of the separation signal for the purpose of removing noises in the above, a value that is greater than 0 and smaller than 1 may be substituted.

The present invention can be employed for the optical measurement instrument for a living body for measuring the living body.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An optical measurement instrument, for a living body, comprising:
a light irradiation unit configured to irradiate a plurality of irradiation points on an object being tested with light;
a light reception unit configured to detect light at a plurality of detection points on said object being tested to derive a plurality of detection signals each representing light transmittance at each of measurement points in said object being tested; and
a calculation unit for calculating hemodynamics of a plurality of factors of each of said measurement points in said object being tested, which includes a first concentration change of oxygenated hemoglobin as a first measurement factor and a second concentration change of deoxygenated hemoglobin as a second measurement factor, from each of the signals derived from said light reception unit, a separation calculation unit for separating a plurality of statistically independent time series signal components from each of said first concentration change and second concentration change by using an independent component analysis method and determining, for each of the separated time series signal components, a first mixing coefficient matrix that indicates how the corresponding time series signal component contributes to the first concentration change of oxygenated hemoglobin at each of said measurement points and a second mixing coefficient matrix that indicates how the corresponding time series signal components contributes to the second concentration change of deoxygenated hemoglobin at each of said measurement points;

a selection unit for calculating, for each of said time series signal components, a correlation coefficient between said first mixing coefficient matrix and said second mixing coefficient matrix to discriminate the corresponding time series signal component as noise signal when said correlation coefficient is a predetermined value or greater as a noise signal; and a reconstruction calculation unit for reconfiguring signals representing hemodynamics of oxygenated hemoglobin and hemodynamics of deoxygenated hemoglobin from the time series signal components excluding the noise signal discriminated by said selection unit.

2. The optical measurement instrument for a living body according to claim 1, wherein said first mixing coefficient matrix and said second mixing coefficient matrix are binarized by a predetermined threshold to calculate the correlation coefficient therebetween.

3. The optical measurement instrument for a living body according to claim 1, wherein said reconstruction calculation unit performs reconstruction by setting the mixing coefficient matrices of the noise signal discriminated by said selection unit as zero.

4. The optical measurement instrument for a living body according to claim 1, wherein said independent component analysis method is a TDDICA method.

5. The optical measurement instrument for a living body according to claim 1, wherein said separation calculation unit performs filtering processing before said separation calculation unit performs the separation calculation.

6. The optical measurement instrument for a living body according to claim 1, wherein said selection unit extracts time series signal components that has a high correlation with the time of the assignment given to said object being tested from the result of separation performed by said separation calculation unit to thereby perform said discrimination from the extraction result.

7. The optical measurement instrument for a living body according to claim 1, wherein said selection unit calculates an instantaneous phase from the separation signals separated by said separation calculation means, selects a signal in which the phase difference between oxygenated hemoglobin and deoxygenated hemoglobin is smaller than a first predetermined value as a body motion noise, and selects a signal in which said difference between the oxygenated hemoglobin and deoxygenated hemoglobin is within a range of a second predetermined value as a brain activity signal.

* * * * *